(12) United States Patent
Bahar

(10) Patent No.: US 7,335,685 B2
(45) Date of Patent: Feb. 26, 2008

(54) CRYSTALS OF LADOSTIGIL TARTRATE, METHODS OF PRODUCTION AND PHARMACEUTICAL COMPOSITIONS THEREOF

(75) Inventor: Eliezer Bahar, Tel-Aviv (IL)

(73) Assignee: TEVA Pharmaceutical Industries, Ltd., Petach-Tikva (IL)

( * ) Notice: Subject to any disclaimer, the term of this patent is extended or adjusted under 35 U.S.C. 154(b) by 156 days.

(21) Appl. No.: 11/359,323

(22) Filed: Feb. 22, 2006

(65) Prior Publication Data

US 2006/0189819 A1 Aug. 24, 2006

Related U.S. Application Data

(60) Provisional application No. 60/656,866, filed on Feb. 24, 2005.

(51) Int. Cl.
*C07C 31/22* (2006.01)
*C07C 271/00* (2006.01)

(52) U.S. Cl. ........................ 514/551; 560/157

(58) Field of Classification Search .................... None
See application file for complete search history.

(56) References Cited

U.S. PATENT DOCUMENTS 3,903,297 A 9/1975 Youdim et al.
6,251,938 B1 6/2001 Chorev et al.
6,303,650 B1 10/2001 Chorev et al.
6,462,222 B1 10/2002 Chorev et al.
6,538,025 B2 3/2003 Chorev et al.
2004/0010038 A1 1/2004 Blaugrund et al.

FOREIGN PATENT DOCUMENTS

WO   WO 98/27055 A1 * 6/1998

OTHER PUBLICATIONS

U.S. Appl. No. 11/091,008, filed Mar. 25, 2005, Chorev et al.
U.S. Appl. No. 11/361,379, filed Feb. 24, 2006, Caciularu et al.
U.S. Appl. No. 11/443,880, filed May 31, 2006, Goren and Blaugrund.
U.S. Appl. No. 60/656,477, filed Feb. 24, 2005, Licht et al.
U.S. Appl. No. 60/686,791, filed Jun. 1, 2005, Goren and Blaugrund.
U.S. Appl. No. 60/700,850, filed Jul. 19, 2005, Goren and Blaugrund.
*Chemical Abstracts Service*, (Columbus, Ohio), Registry No. 209394-46-7.
Sterling et al., Journal of Medicinal Chemistry, 2002, vol. 45, pp. 5260-5279.

* cited by examiner

*Primary Examiner*—Paul A. Zucker
(74) *Attorney, Agent, or Firm*—John P. White; Cooper & Dunham LLP

(57) ABSTRACT

Disclosed is crystalline ladostigil tartrate of a specified density, compositions, including pharmaceutical compositions comprising such ladostigil tartrate, and a process for the manufacture thereof.

25 Claims, 6 Drawing Sheets

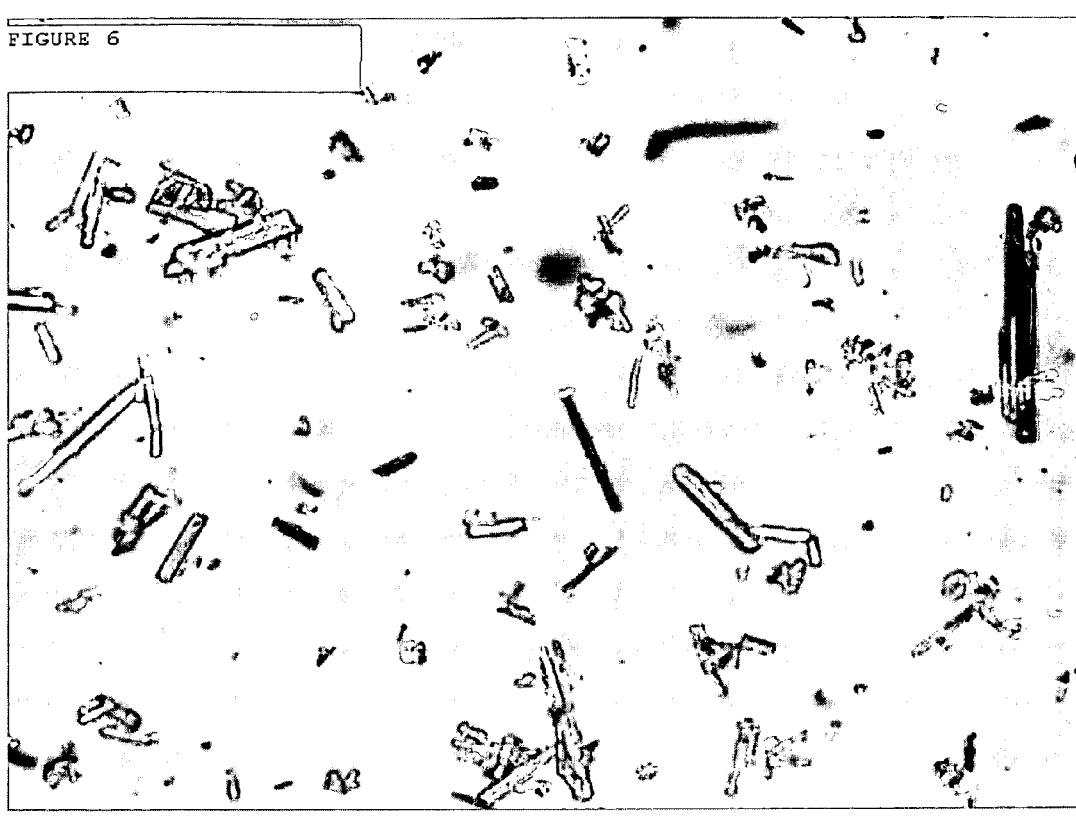

CRYSTALS OF LADOSTIGIL TARTRATE, METHODS OF PRODUCTION AND PHARMACEUTICAL COMPOSITIONS THEREOF

This application claims the benefit of U.S. Provisional Application No. 60/656,866, filed Feb. 24, 2005, the entire contents of which are hereby incorporated by reference.

Throughout this application various publications, published patent applications, and published patents are referenced. The disclosures of these publications in their entireties are hereby incorporated by reference into this application in order to more fully describe the state of the art to which this invention pertains.

BACKGROUND OF THE INVENTION

PCT Application Publication No. WO98/27055 discloses indanylamine and aminotetralin compounds, such as those of Formula I below, which are useful to treat dementias, depression, Attention Deficit Disorder (ADD), Attention Deficit and Hyperactivity Disorder (ADHD), Tourette's Syndrome, Alzheimer's Disease and other disorders. The indanylamine derivatives disclosed have been shown to have biological effects in animal models of neurological disease. In addition, PCT Application Publication No. WO98/27055 discloses methods for preparation of such compounds.

Formula I:

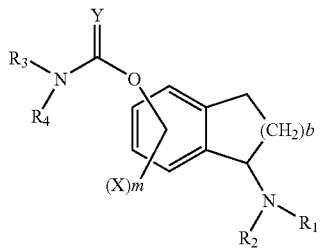

wherein b is 1 or 2; m is 0-3; Y is O or S; X is halo; $R_1$ is hydrogen or $C_{1-4}$ alkyl; $R_2$ is hydrogen, $C_{1-4}$ alkyl, or optionally substituted propargyl; and $R_3$ and $R_4$ are each independently hydrogen, $C_{1-8}$ alkyl, $C_{6-12}$ aryl, $C_{6-12}$ aralkyl, each optionally halo substituted.

R(+)-6-(N-methyl,N-ethyl-carbamoyloxy)-N'-propargyl-1-aminoindan, also known as (3R)-3-(prop-2-ynylamino)-2,3,-dihydro-1H-inden-5-yl ethylmethylcarbamate, and carbamic acid, ethylmethyl-, (3R)-2,3-dihydro-3-(2-propynylamino)-1H-inden-5-yl ester, is disclosed in PCT Application Publication No. WO98/27055, specifically compound 76 in Table 5. In addition, salts are disclosed, including the ½ L-tartrate salt. This salt has been given the nonproprietary name ladostigil tartrate. Its CAS registry number is 209394-46-7.

PCT Application Publication No. WO98/27055 describes laboratory scale preparations of its compounds. Thus, PCT Application Publication No. WO98/27055 does not disclose whether and how any of the compounds can be prepared on a larger scale, such as in a pilot plant and production plant.

SUMMARY OF THE INVENTION

Disclosed is a scaled-up process for the preparation of ladostigil tartrate which also surprisingly results in rod-shaped crystals of higher density, which when used in the formulation of a pharmaceutical composition, i.e., a drug product, provides beneficial uniformity of content of the drug product.

The subject invention provides a crystalline R(+)-6-(N-methyl, N-ethyl-carbamoyloxy)-N'-propargyl-1-aminoindan ½ L-tartrate having a tapped density of at least 0.300 g/ml.

The subject also provides a composition comprising crystalline R(+)-6-(N-methyl, N-ethyl-carbamoyloxy)-N'-propargyl-1-aminoindan ½ L-tartrate having a tapped density of at least 0.300 g/ml.

BRIEF DESCRIPTION OF FIGURES

FIG. 6: Crystals prepared by a crystal breeding method after milling (Batch DM), 20× magnification in mineral oil

DETAILED DESCRIPTION OF THE INVENTION

Figure 1:
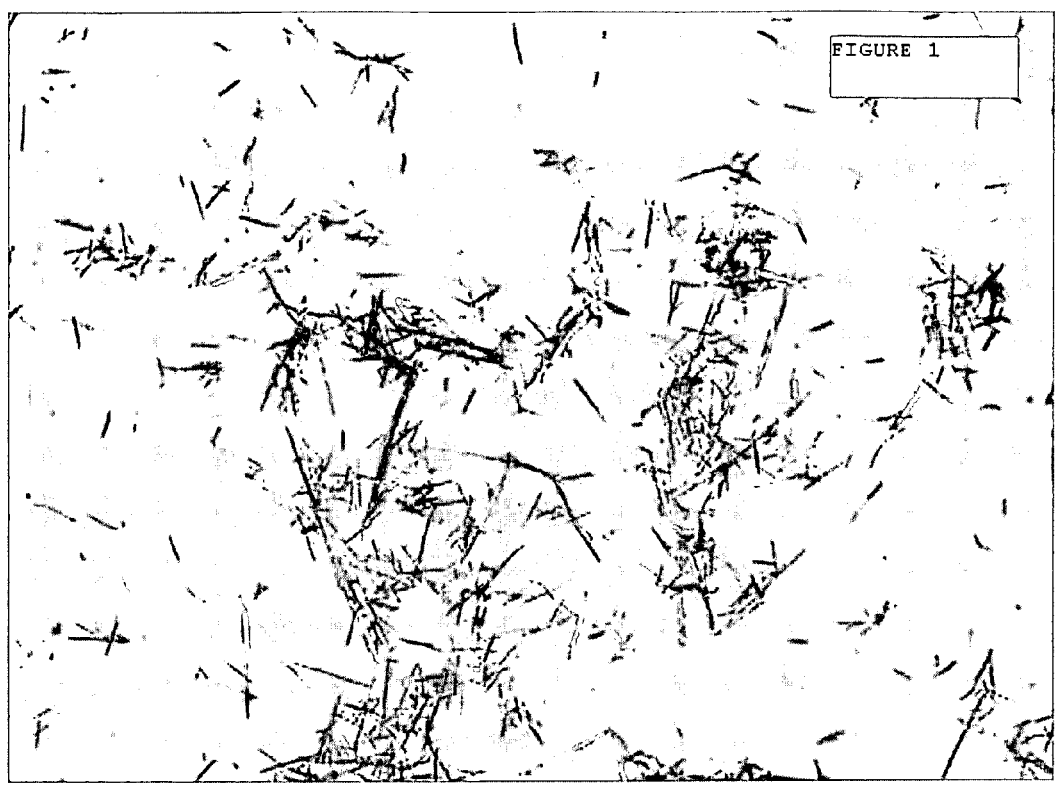
FIG. 1: Crystals prepared by a process that includes recrystallization method before milling (Batch ZU), 10× magnification in mineral oil

The subject invention provides crystalline R(+)-6-(N-methyl, N-ethyl-carbamoyloxy)-N'-propargyl-1-aminoindan ½ L-tartrate having a tapped density of at least 0.300 g/ml.

In a further embodiment, the crystalline R(+)-6-(N-methyl, N-ethyl-carbamoyloxy)-N'-propargyl-1-aminoindan ½ L-tartrate has a tapped density of at least 0.400 g/ml.

In a further embodiment, the crystalline R(+)-6-(N-methyl, N-ethyl-carbamoyloxy)-N'-propargyl-1-aminoindan ½ L-tartrate has a tapped density of at least 0.500 g/ml.

In a further embodiment, the crystalline R(+)-6-(N-methyl, N-ethyl-carbamoyloxy)-N'-propargyl-1-aminoindan ½ L-tartrate of has a bulk density of at least 0.200 g/ml.

In a further embodiment, the crystalline R(+)-6-(N-methyl, N-ethyl-carbamoyloxy)-N'-propargyl-1-aminoindan ½ L-tartrate has a bulk density of at least 0.250 g/ml.

In a further embodiment, the crystalline R(+)-6-(N-methyl, N-ethyl-carbamoyloxy)-N'-propargyl-1-aminoindan ½ L-tartrate has a tapped density of less than 0.600 g/ml.

The subject invention also provides a composition comprising crystalline R(+)-6-(N-methyl, N-ethyl-carbamoyloxy)-N'-propargyl-1-aminoindan ½ L-tartrate having a tapped density of at least 0.300 g/ml.

In a further embodiment, the R(+)-6-(N-methyl, N-ethyl-carbamoyloxy)-N'-propargyl-1-aminoindan ½ L-tartrate has a tapped density of at least 0.400 g/ml.

In a further embodiment, the R(+)-6-(N-methyl, N-ethyl-carbamoyloxy)-N'-propargyl-1-aminoindan ½ L-tartrate has a tapped density of at least 0.500 g/ml.

In a further embodiment, the R(+)-6-(N-methyl, N-ethyl-carbamoyloxy)-N'-propargyl-1-aminoindan ½ L-tartrate has a bulk density of at least 0.200 g/ml.

In a further embodiment, the R(+)-6-(N-methyl, N-ethyl-carbamoyloxy)-N'-propargyl-1-aminoindan ½ L-tartrate has a bulk density of at least 0.250 g/ml.

In a further embodiment, the R(+)-6-(N-methyl, N-ethyl-carbamoyloxy)-N'-propargyl-1-aminoindan ½ L-tartrate has a tapped density of less than 0.600 g/ml.

In a further embodiment, the composition is a pharmaceutical composition comprising a pharmaceutically acceptable carrier.

In a further embodiment, the pharmaceutical composition is in the form of a tablet, capsule, pill, powder or granule.

In a further embodiment, the pharmaceutical composition is in tablet form.

In a further embodiment, the pharmaceutical composition comprises a coating.

In a further embodiment, a process for the making the crystalline R(+)-6-(N-methyl, N-ethyl-carbamoyloxy)-N'-propargyl-1-aminoindan ½ L-tartrate or the composition comprises:

a) obtaining a solution of R(+)-6-(N-methyl, N-ethyl-carbamoyloxy)-N'-propargyl-1-aminoindan in isopropanol at a temperature of 50° C.-70° C.;

b) obtaining a solution of L-tartaric acid in isopropanol at a temperature of 50° C.-70° C.;

c) combining the solution of step b) with the solution of step a) at a rate such that the solutions are combined at 1.5-5 hours after initiation of the combining step, and at a temperature of 50° C.-70° C. to form a combined solution;

d) maintaining the combined solution at a temperature of 50° C.-70° C. for a period of 4-24 hours;

e) cooling the combined solution at the rate of 10° C.-15° C. per hour to form a precipitate;

f) isolating the precipitate.

In a further embodiment, the rate in step c) is such that the solutions are combined 2.5-3.5 hours after initiation of step c).

In a further embodiment, step c) is performed at a temperature of 60° C.-65° C.

In a further embodiment, the combining in step c) is performed dropwise.

In a further embodiment, the period of time in step d) is 4-15 hours.

In a further embodiment, the rate of cooling in step e) is 12° C. per hour.

In a further embodiment, the solution of step a) is heated to a temperature of 60-65° C.

In a further embodiment, in step e) the cooling is to a temperature of 0-5° C.

In a further embodiment, the process further comprises the step of seeding the solution of step a) with crystalline ladostigil tartrate before performing step c).

As used herein, a "pharmaceutically acceptable" component is one that is suitable for use with humans and/or animals without undue adverse side effects (such as toxicity, irritation, and allergic response) commensurate with a reasonable benefit/risk ratio.

Thus, a "pharmaceutically acceptable carrier" is a pharmaceutically acceptable solvent, suspending agent or vehicle, for delivering the instant compounds to the animal or human. The carrier is selected with the planned manner of administration in mind. Liposomes are also a pharmaceutical carrier.

A dosage unit may comprise a single compound or mixtures of compounds thereof. A dosage unit can be prepared for oral dosage forms, such as tablets, capsules, pills, powders, and granules.

The drug substance can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. The drug substance can be administered alone but are generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of pharmaceutical acceptable carriers and excipients that may be used to formulate oral dosage forms of the present invention are described, e.g., in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

As used herein, "density" is a measurement defined as the mass of a substance per unit volume.

As used herein, "bulk density" refers to a density measurement of a loose, uncompacted substance, wherein the volume of the substance includes the air trapped between particles.

As used herein, "tapped density" refers to a density measurement of a substance that has been tapped or vibrated, thus minimizing the volume of the substance by eliminating or minimizing the air trapped between particles.

As used herein, "aspect ratio" is the quotient of the division of a crystal's length by its width.

Experimental Details: Materials and Methods

Bulk Density, Tapped Density and Aspect Ratio

The bulk density, tapped density and aspect ratio of the batches of ladostigil tartrate crystals were determined using the following methods:

Bulk Density (BD)
1. Mix powder;
2. Tare a 100 ml empty cylinder on a 0.01 g sensitivity balance;
3. Transfer the powder, without compacting, to the cylinder being held at approximately 45 degree angle to achieve an untapped apparent volume of 60 to 100 ml;
4. Bring the cylinder containing the sample to a vertical position by a sharp move in order to level the volume for reading.
5. Read the apparent volume (Va) to the nearest graduated unit;
6. Weigh the cylinder with sample (the balance gives sample weight (M);
7. Calculate bulk density in g/ml according to the following equation:

$BD=M/Va$;

8. Perform steps 1-7 again and report the average data of duplicates.

Tapped Density (TD)
1. Put the same cylinder used to calculate Bulk Density in a Quantachrome Dual Autotap instrument;
2. Perform 1250 taps;
3. Read the tapped volume (Vf) to the nearest graduated unit;
4. Calculate the tapped density in g/ml according to the following equation:

$TD=M/Vf$;

5. Perform steps 1-4 again and report the average data of duplicates.

Aspect Ratio

Slides were prepared and micrographs were taken of each batch. Each micrograph was divided into five fields. The length and width of 20 representative crystals in each field were measured. The aspect ratio of each crystal was calculated by dividing the crystal length by the crystal width. The average aspect ratio for each batch was determined by dividing the sum of crystal aspect ratios by the number of crystals measured. The results are reported as an average of at least two measurements per sample.

EXAMPLE 1

Method of Preparing Crystals of Ladostigil Tartrate in Isopropanol (Following Disclosure of PCT Application Publication No. WO98/27055)

PCT Application Publication No. WO98/27055 discloses the production of 6-(N,N-dimethylcarbamyloxy)-N-propargyl aminoindan mesylate. In this manner ladostigil tartrate was prepared in WO98/27055. The following preparation of ladostigil tartrate follows the described method for the mesylate salt of 6-(N,N-dimethylcarbamyloxy)-N-propargyl aminoindan, except for the use of 1) L-Tartaric acid in isopropanol instead of methanesulfonic acid in ether, 2) R(+)-6-(N-methyl, N-ethyl-carbamoyloxy)-N'-propargyl-1-aminoindan instead of 6-(N,N-dimethylcarbamyloxy)-N-propargyl aminoindan HCl, and 3) use of larger amounts of reagents: 195 grams of R(+)-6-(N-methyl, N-ethyl-carbamoyloxy)-N'-propargyl-1-aminoindan and 7.09 liters of isopropanol (36.3 volumes) were introduced into a 6 liter jacketed reactor equipped with a mechanical stirrer and a thermometer. A solution of L-Tartaric acid (59.1 g, 0.394 mol) in iso-propanol (1.18 liters, 6.0 volumes) was added dropwise at 25° C. to the solution during 15 minutes. The resulting suspension was stirred for 30 minutes and allowed to settle for 30 minutes. The material formed was collected by filtration and dried under vacuum at 50° C. to give 169.7 gram (68.2%) of crystalline material (Batch GA). The bulk density and tapped density were measured.

EXAMPLE 2

Recrystallization of Ladostigil Tartrate in Isopropanol (Following Disclosure of PCT Application Publication No. WO98/27055)—Unmilled PCT Application Publication No. WO98/27055 also teaches recrystallizing the mesylate salt of 6-(N,N-dimethylcarbamyloxy)-N-propargyl aminoindan. Thus, the following was done:

240 grams of ladostigil tartrate and 2.4 liters of isopropanol (10 volumes) were introduced into a 3 liter jacketed reactor equipped with a mechanical stirrer and a thermometer. The mixture was heated to 74° C. (jacket temperature 95° C.) until a clear solution was obtained. The solution was cooled gradually. At 55° C., (reactor content temperature) a very fast crystallization occurred. Cooling was continued until the reactor content temperature reached 7° C. The reactor was discharged and the crystals were collected by filtration and washed with cold isopropanol (0.4 liters). The wet material was dried in a vacuum oven at 50° C. to give 224 grams (93.3%) of crystalline material (Batch ZU, FIG. 1). The aspect ratio, bulk density, and tapped density were measured.

EXAMPLE 3

Figure 2:
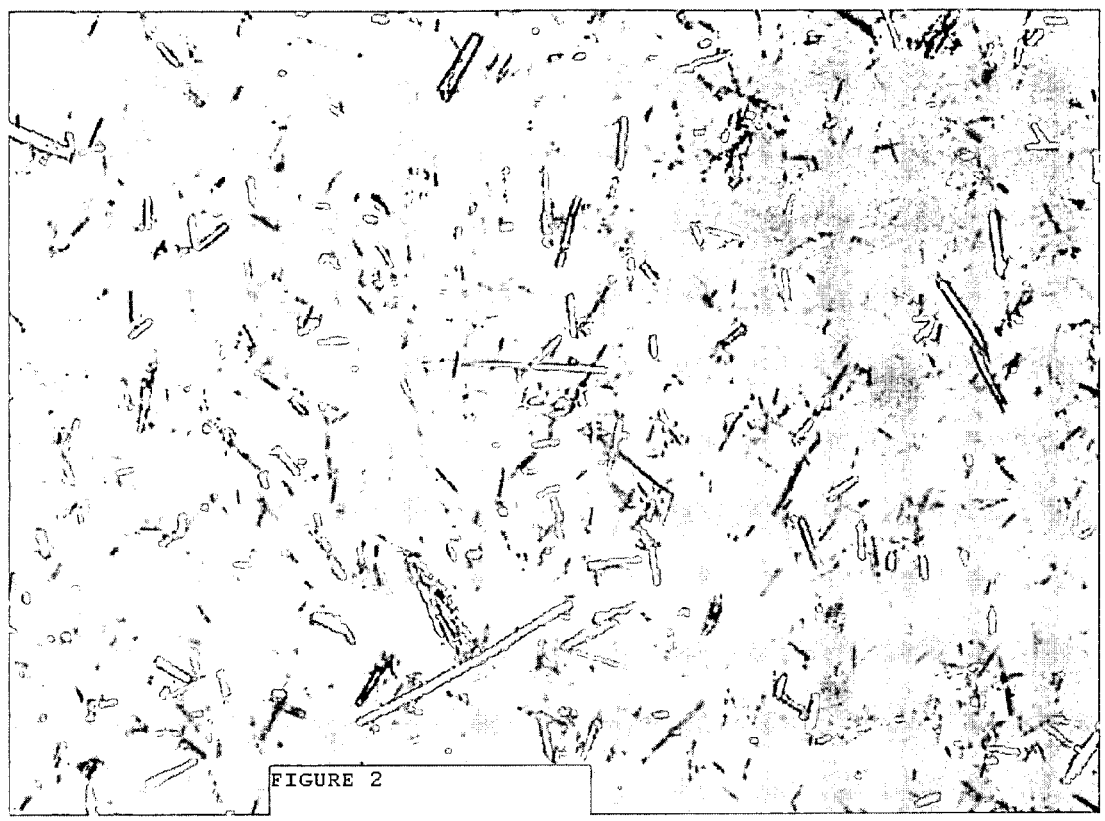
FIG. 2: Crystals prepared by a process that includes recrystallization method after milling (Batch ZM), 10× magnification in mineral oil
Figure 3:
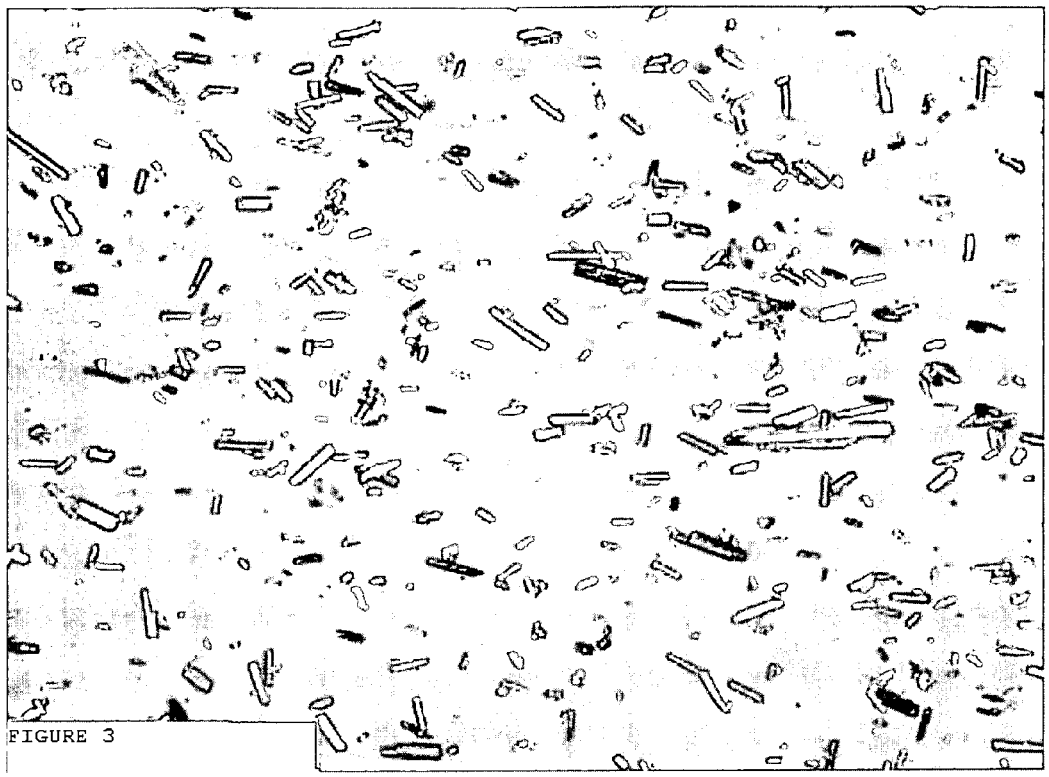
FIG. 3: Crystals prepared by a crystal breeding method before milling (Batch CU), 10× magnification in mineral oil
Figure 4:
FIG. 4: Crystals prepared by a crystal breeding method before milling (Batch DU), 10× magnification in mineral oil
Figure 5:
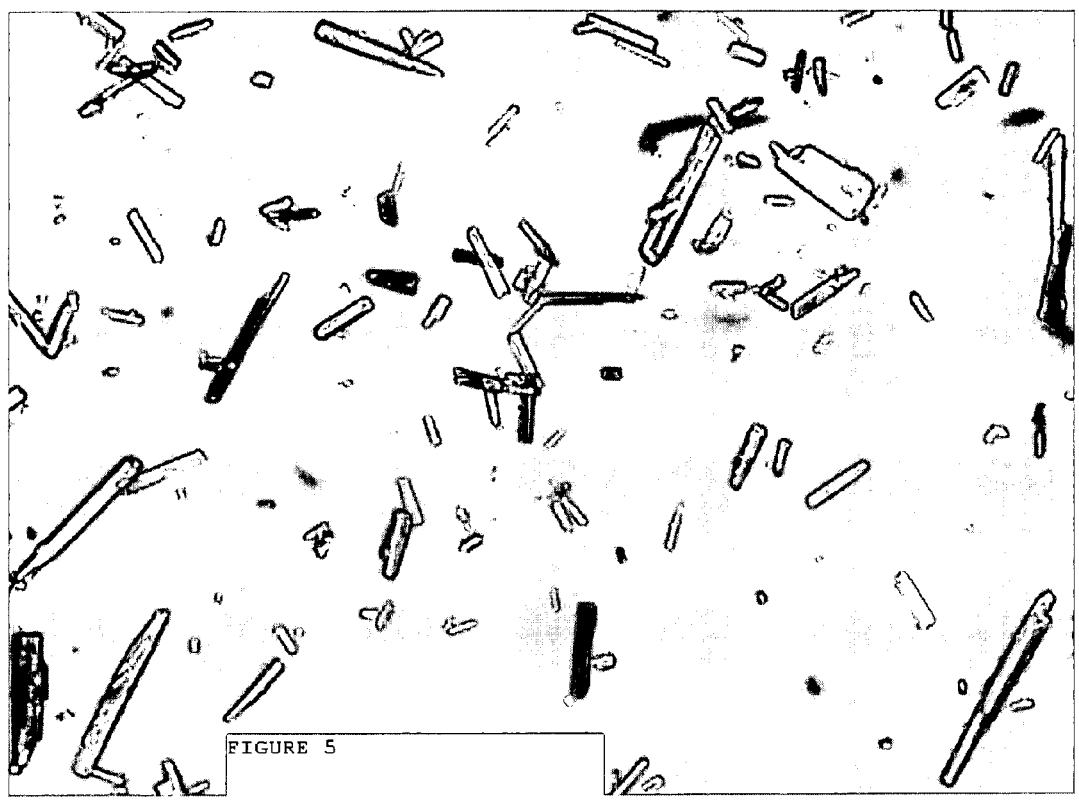
FIG. 5: Crystals prepared by a crystal breeding method after milling (Batch CM), 20× magnification in mineral oil

Recrystallization of Ladostigil Tartrate in Isopropanol (Following Disclosure of PCT Application Publication No. WO98/27055)—Milled Alternatively, the dried material produced in Example 2 was milled after drying in a Comil 197 Double screen 018R 6000 rpm (Batch ZM, FIG. 2). The aspect ratio, bulk density and tapped density of the milled product were measured.

EXAMPLE 4

Crystal Breeding Method of Ladostigil Tartrate in Isopropanol, Method A—Unmilled In a 250 liter reactor, a solution of R(+)-6-(N-methyl, N-ethyl-carbamoyloxy)-N'-propargyl-1-aminoindan (8.3 kg) in isopropanol (52.4 liters) was heated to 60-65° C. The solution was seeded with 50 g of ladostigil tartrate and a solution of L-tartaric acid (2.4 kg) in isopropanol (38.5 liters) was added dropwise over 2.5-3.5 hours. The mixture was maintained at 60-65° C. for 4-15 hr and was then gradually cooled to 0-5° C. over a period of 6 hours. The product was collected in a Guedu FD-2 filter drier and was washed with cold isopropanol (77 liters). The wet material was dried in a filter drier in three stages until moisture content was less than 0.5%. In the first drying stage, the product was dried by static drying for 4 hours at 50-60° C. and under vacuum of less than 50 mbar. In the second drying stage, the product was dried while being stirred for 2 hours at 50-60° C. and under vacuum of less than 50 mbar. In the third drying stage the product was dried while being stirred for 2 hours at 78-82° C. and under vacuum of less than 50 mbar. Two batches of dried ladostigil tartrate (9.67 kg) were obtained (Batches CU and DU). The aspect ratio, bulk density, and tapped density were measured.

EXAMPLE 5

Crystal Breeding Method of Ladostigil Tartrate in Isopropanol, Method A—Milled

Alternatively, the dried material from both batches produced in Example 4 were milled in a Comil 197 Double screen 018R 6000 rpm (Batches CM and DM). The aspect ratio, bulk density, and tapped density of each milled batch were measured.

EXAMPLE 6

Crystal Breeding Method of Ladostigil Tartrate in Isopropanol, Method B—Unmilled The same procedure as in method A (Example 4) was performed, however, the seeding step was not performed. Ladostigil tartrate (Batch EU) was attained. The bulk density and tapped density were measured.

EXAMPLE 7

Crystal Breeding Method of Ladostigil Tartrate in Isopropanol, Method B—Milled

Alternatively, the dried material produced in Example 6 was milled in a Comil 197 Double screen 018R 6000 rpm (Batch EM). The bulk density and tapped density of the milled product were measured.

Results

TABLE 1

| Method of production | Batch | BD (g/ml) | TD (g/ml) |
|---|---|---|---|
| Preparation method following PCT Application Publication No. WO98/27055 (Example 1) | GA | 0.220 | 0.283 |
| With recrystallization method before milling (Example 2) | ZU | 0.130 | 0.185 |
| With recrystallization method after milling (Example 3) | ZM | 0.097 | 0.154 |
| Crystal breeding method A before milling (Example 4) | CU | 0.290 | 0.535 |
| Crystal breeding method A before milling (Example 4) | DU | 0.245 | 0.450 |
| Crystal breeding method B before milling (Example 6) | EU | 0.215 | 0.377 |
| Crystal breeding method A after milling (Example 5) | CM | 0.272 | 0.508 |
| Crystal breeding method A after milling (Example 5) | DM | 0.227 | 0.430 |
| Crystal breeding method B after milling (Example 7) | EM | 0.218 | 0.350 |

TABLE 2

| Method of production | Batch | Aspect Ratio |
|---|---|---|
| With recrystallization method before milling (Example 2) | ZU | 9 |
| With recrystallization method after milling (Example 3) | ZM | 7 |
| Crystal breeding method A before milling (Example 4) | CU | 5 |
| Crystal breeding method A before milling (Example 4) | DU | 6 |
| Crystal breeding method A after milling (Example 5) | CM | 6 |
| Crystal breeding method A after milling (Example 5) | DM | 6 |

Discussion of Results

Ladostigil tartrate is disclosed in PCT Application Publication No. WO98/27055. However, two methods of its preparation are possible, depending upon whether the starting material is the racemic or the R(+) form of 6-(N-methyl, N-ethyl-carbamoyloxy)-N'-propargyl-1-aminoindan.

Ladostigil tartrate prepared using racemic 6-(N-methyl, N-ethyl-carbamoyloxy)-N'-propargyl-1-aminoindan as the starting material would require recrystallization in order to purify the desired R(+) enantiomer. Although L-tartaric acid is chiral and preferentially forms a salt with the R(+) form of 6-(N-methyl,N-ethyl-carbamoyloxy)-N'-propargyl-1-aminoindan, recrystallization is required to purify the R(+) form because some S(−) enantiomer does form despite the preference.

Furthermore, an attempt to scale-up the laboratory scale preparation method derived from PCT Application Publication No. WO98/27055 proved problematic. When the method for producing ladostigil tartrate derived from PCT Application Publication No. WO98/27055 was scaled-up, rapid crystallization prevented stirring in the reactor. Up to half of the reaction product formed as a large, solid mass of long, needle-shaped crystals. The crystal mass did not drain from the bottom of the reactor, and it was otherwise difficult to remove the reaction product from the reactor. Thus, a new process was required for producing ladostigil tartrate on a pilot and production scale.

Examples 4-7 describe a new crystal breeding method of preparing ladostigil tartrate, which is the subject of the present invention. Ladostigil tartrate can be prepared by the crystal breeding method in a 250-liter jacket without forming a large mass of crystals. Thus, it is not prone to the scale-up problems inherent in methods derived from PCT Application Publication No. WO98/27055.

The crystal breeding method of Examples 4-7 was surprisingly found to have several additional benefits. Specifically, Table 1 shows that the bulk density and tapped density values of ladostigil tartrate as prepared in Examples 1-3 are low. Low tapped density is anathema to certain prized qualities in a drug substance such as compressibility, the ability of a powder to decrease in volume under pressure, and compactibility, the ability of a powder to be compressed into a tablet of certain strength or hardness. Crystals with low tapped density are also known to have poor flowability, which results in a lack of uniformity of content in finished dosage forms, especially tablets. (Rudnic et al. Chpt. 45, *Remington's Pharmaceutical Sciences*, 20$^{th}$ Edition, Lippincott Williams & Wilkins, Baltimore, Md. (2000)) Moreover, the storage space required for raw material, e.g., a drug substance, with lower density is greater than storage space required for a material with a higher density. The increase in storage space increases the production costs.

Example 3 describes a method of milling the ladostigil tartrate produced in Example 2. As shown in Table 1, however, milling changes significantly neither the bulk density nor the tapped density of recrystallized ladostigil tartrate.

Ladostigil tartrate prepared using R(+)6-(N-methyl,N-ethyl-carbamoyloxy)-N'-propargyl-1-aminoindan as the starting material, as described in Example 1, exhibits a better bulk density in comparison to the ladostigil tartrate of Example 2. Nevertheless, the tapped density value of Example 1 remains low. Higher bulk density does little to alleviate the processability problems mentioned above, however. Tapped density is the prime value upon which drug substances like ladostigil tartrate are graded.

In contrast, the bulk and tapped density values of ladostigil tartrate as prepared in Examples 4-7 are higher than those prepared in Examples 1-3. As such, crystals produced by the crystal breeding method provide a better quality of drug substance in terms of compressibility, compactibility and flowability.

Another benefit of the crystal breeding method is that the ladostigil tartrate crystals are rod-shaped as opposed to the needle-shaped crystals produced by recrystallization, as seen in FIGS. 1-6. Needle-shaped crystals have been shown to cause processability problems when making pharmaceutical compositions using conventional tableting devices. For example, needle-shaped crystals are often difficult to coat, thereby precluding their use in controlled release pharmaceutical dosage forms. (Porter, Stuart C. Chpt. 46, *Remington's, infra.*) Rod-shaped crystals, on the other hand, do not suffer from such limitations.

The methods for making ladostigil tartrate disclosed in the prior art are not conducive to scale-up, and the prior art crystals of ladostigil tartrate do not achieve the high density values of the present invention. As such, ladostigil tartrate prepared by the disclosed crystal breeding method is better suited for use in pharmaceutical preparations.

What is claimed:

1. Crystalline R(+)-6-(N-methyl, N-ethyl-carbamoyloxy)-N'-propargyl-1-aminoindan ½ L-tartrate having a tapped density of at least 0.300 g/ml.

2. The crystalline R(+)-6-(N-methyl, N-ethyl-carbamoyloxy)-N'-propargyl-1-aminoindan ½ L-tartrate of claim 1, having a tapped density of at least 0.400 g/ml.

3. The crystalline R(+)-6-(N-methyl, N-ethyl-carbamoyloxy)-N'-propargyl-1-aminoindan ½ L-tartrate of claim 1, having a tapped density of at least 0.500 g/ml.

4. The crystalline R(+)-6-(N-methyl, N-ethyl-carbamoyloxy)-N'-propargyl-1-aminoindan ½ L-tartrate of claim 1, having a bulk density of at least 0.200 g/ml.

5. The crystalline R(+)-6-(N-methyl, N-ethyl-carbamoyloxy)-N'-propargyl-1-aminoindan ½ L-tartrate of claim 4, having a bulk density of at least 0.250 g/ml.

6. The crystalline R(+)-6-(N-methyl, N-ethyl-carbamoyloxy)-N'-propargyl-1-aminoindan ½ L-tartrate of claim 1, having a tapped density of less than 0.600 g/ml.

7. A composition comprising crystalline R(+)-6-(N-methyl, N-ethyl-carbamoyloxy)-N'-propargyl-1-aminoindan ½ L-tartrate having a tapped density of at least 0.300 g/ml.

8. The composition of claim 7, wherein the R(+)-6-(N-methyl, N-ethyl-carbamoyloxy)-N'-propargyl-1-aminoindan ½ L-tartrate has a tapped density of at least 0.400 g/ml.

9. The composition of claim 8, wherein the R(+)-6-(N-methyl, N-ethyl-carbamoyloxy)-N'-propargyl-1-aminoindan ½ A L-tartrate has a tapped density of at least 0.500 g/ml.

10. The composition of claim 7, wherein the R(+)-6-(N-methyl, N-ethyl-carbamoyloxy)-N'-propargyl-1-aminoindan ½ L-tartrate has a bulk density of at least 0.200 g/ml.

11. The composition of claim 10, wherein the R(+)-6-(N-methyl, N-ethyl-carbamoyloxy)-N'-propargyl-1-aminoindan ½ L-tartrate has a bulk density of at least 0.250 g/ml.

12. The composition of claim 7, wherein the R(+)-6-(N-methyl, N-ethyl-carbamoyloxy)-N'-propargyl-1-aminoindan ½ L-tartrate has a tapped density of less than 0.600 g/ml.

13. The composition of claim 7 wherein the composition is a pharmaceutical composition comprising a pharmaceutically acceptable carrier.

14. The pharmaceutical composition of claim 13 in the form of a tablet, capsule, pill, powder or granule.

15. The pharmaceutical composition of claim 14 in tablet form.

16. The pharmaceutical composition of claim 14 comprising a coating.

17. A process for the making the crystalline R(+)-6-(N-methyl, N-ethyl-carbamoyloxy)-N'-propargyl-1-aminoindan ½ L-tartrate of claim 1 comprising:
  a) obtaining a solution of R(+)-6-(N-methyl, N-ethyl-carbamoyloxy)-N'-propargyl-1-aminoindan in isopropanol at a temperature of 50° C.-70° C.;
  b) obtaining a solution of L-tartaric acid in isopropanol;
  c) combining the solution of step b) with the solution of step a) at a rate such that the solutions are combined at 1.5-5 hours after initiation of the combining step, and at a temperature of 50° C.-70° C. to form a combined solution;
  d) maintaining the combined solution at a temperature of 50° C.-70° C. for a period of 4-24 hours;
  e) cooling the combined solution at the rate of 10° C.-15° C. per hour to form a precipitate;
  f) isolating the precipitate.

18. The process of claim 17, wherein the rate in step c) is such that the solutions are combined 2.5-3.5 hours after initiation of step c).

19. The process of claim 17, wherein step c) is performed at a temperature of 60° C.-65° C.

20. The process of claim 17, wherein the combining in step c) is performed dropwise.

21. The process of claim 17, wherein the period of time in step d) is 4-15 hours.

22. The process of claim 17, wherein the rate of cooling in step e) is 12° C. per hour.

23. The process of claim 17, wherein the solution of step a) is heated to a temperature of 60-65° C.

24. The process of claim 17, wherein in step e) the cooling is to a temperature of 0-5° C.

25. The process of claim 17, further comprising the step of seeding the solution of step a) with crystalline ladostigil tartrate before performing step c).

* * * * *